United States Patent
Yu et al.

(10) Patent No.: US 8,946,974 B2
(45) Date of Patent: Feb. 3, 2015

(54) PIEZOELECTRIC POLYMER FIBERS

(75) Inventors: Michael Yu, Timonium, MD (US); Dawnielle Farrar, Randallstown, MD (US); Wonkyu Moon, Kyungbuk (KR); James West, Plainfield, NJ (US); Sangkyu Lee, Kyungbuk (KR)

(73) Assignee: The Johns Hopkins University, Baltimore, MD (US)

( * ) Notice: Subject to any disclaimer, the term of this patent is extended or adjusted under 35 U.S.C. 154(b) by 566 days.

(21) Appl. No.: 13/057,652

(22) PCT Filed: Aug. 19, 2009

(86) PCT No.: PCT/US2009/054326
§ 371 (c)(1),
(2), (4) Date: Feb. 4, 2011

(87) PCT Pub. No.: WO2010/022158
PCT Pub. Date: Feb. 25, 2010

(65) Prior Publication Data
US 2011/0260584 A1  Oct. 27, 2011

Related U.S. Application Data

(60) Provisional application No. 61/090,060, filed on Aug. 19, 2008.

(51) Int. Cl.
*H01L 41/083* (2006.01)
*D01F 6/68* (2006.01)
(Continued)

(52) U.S. Cl.
CPC ............... *D01F 6/68* (2013.01); *D01D 5/0038* (2013.01); *G01N 29/2437* (2013.01); *H01L 41/193* (2013.01); *H01L 41/082* (2013.01)
USPC .................................. 310/358; 252/62.9 PZ

(58) Field of Classification Search
USPC .......................... 310/800, 358, 328, 311, 357
IPC ............................................ H01L 41/08,41/083
See application file for complete search history.

(56) References Cited

U.S. PATENT DOCUMENTS 2,486,560 A  11/1949  Gray
2,708,244 A   5/1955  Jaffe
(Continued)

FOREIGN PATENT DOCUMENTS

JP     7-327297 A     12/1995
JP  2001-282140 A     10/2001
(Continued)

OTHER PUBLICATIONS (A review on polymer nanofiber by electrospinning and their application in nanocomposite. Science direct; composite Science Technology 63(2003) p. 2223-2253).*

(Continued)

*Primary Examiner* — Thomas Dougherty
*Assistant Examiner* — Karen B Addison
(74) *Attorney, Agent, or Firm* — Venable LLP; Henry J. Daley; Daniel A. Kopp

(57) ABSTRACT

Piezoelectric fibers include a polypeptide wherein molecules of the polypeptide have electric dipole moments that are aligned such that the piezoelectric fiber provides a piezoelectric effect at an operating temperature. A piezoelectric component provides a plurality of piezoelectric fibers, each comprising an organic polymer. A method of producing piezoelectric fibers includes electrospinning a polymer solution to form a fiber and winding the fiber onto a rotating target in which the rotating target is electrically grounded. An acoustic sensor includes a plurality acoustic transducers, wherein the plurality of acoustic transducers are structured and arranged to detect a corresponding plurality of vector components of an acoustic signal, and at least one of the plurality of acoustic transducers comprises a piezoelectric fiber.

22 Claims, 14 Drawing Sheets

(51) Int. Cl.
*D01D 5/00* (2006.01)
*G01N 29/24* (2006.01)
*H01L 41/193* (2006.01)
*H01L 41/08* (2006.01)

(56) References Cited

U.S. PATENT DOCUMENTS

| | | | |
|---|---|---|---|
| 5,298,602 | A | 3/1994 | Shikinami et al. |
| 5,494,617 | A | 2/1996 | Iwamoto |
| 7,045,075 | B2 | 5/2006 | Kasukawa et al. |
| 7,101,491 | B2 | 9/2006 | Nonoyama et al. |
| 2006/0198760 | A1* | 9/2006 | Potyrailo et al. ............ 422/82.01 |
| 2007/0200460 | A1* | 8/2007 | Scott ............................ 310/334 |
| 2011/0260584 | A1 | 10/2011 | Yu et al. |
| 2014/0117272 | A1* | 5/2014 | Yu et al. .................. 252/62.9 R |

FOREIGN PATENT DOCUMENTS

| | | | | |
|---|---|---|---|---|
| WO | WO-2008005820 | A2 | 1/2008 | |
| WO | WO-2008/021191 | A2 | 2/2008 | |
| WO | WO 2008021191 | * | 2/2008 | .............. B32B 27/30 |
| WO | WO-2009013376 | A1 | 1/2009 | |
| WO | WO-2010/022158 | A2 | 2/2010 | |
| WO | WO-2010104196 | A1 | 9/2010 | |

OTHER PUBLICATIONS

Benjamin, K., (2002) Recent Advances in 1-3 Piezoelectric Polymer Composite Transducer Technology for AUV/UUV Acoustic Imaging Applications. Journal of Electroceramics, vol. 8, pp. 145-154.
Deming et al. (1997) Facile synthesis of block copolypeptides of defined architecture. Nature, vol. 390, pp. 386-389.
Fleury et al., (1996) Improvements of Ultrasonic Inspections through the Use of Piezo-Composite Transducers (translated into english from the original paper—May 1995). Transducer Workshop, NDTnet, vol. 1, No. 09.
Gerhard-Multhaupt, R. (2002) Voided polymer electrets—New materials, new challenges, new chances. 11th International Symposium on Electrets, pp. 36-45.
Honda et al., (2008) Electrically Controlled Piezoelectric Motion of Piezoelectric Chiral Polymeric Fibers. Japanese Journal of Applied Physics, vol. 47, No. 9, pp. 7642-7645.
Honda et al., (2007) Piezoelectricity of Chiral Polymeric Fibers. Japanese Journal of Applied Physics, vol. 46, No. 10B, pp. 7122-7124.
Kawai, H., (1969) The Piezoelectricity of Poly(vinylidene Fluoride). Japan J. Appl. Phys., vol. 8, pp. 975-976.
Minato et al., (2006) Chain Conformations of Poly(y-benzyl-L-glutamate) Pre and Post an Electrospinning Process. Macromolecular Bioscience, vol. 6, pp. 487-495.
Sessler et al., (1962) Self-Based Conderser Microphone with High Capacitance. The Journal of the Acoustical Society of America, vol. 34, No. 11, pp. 1787-1788.
Tajitsu et al., (2004) Microactuators with Piezoelectric Polylactic Acid Fibers—Toward the Realization of Tweezers for Biological Cells. Taylor & Francis, vol. 304, pp. 195-200.
Tajitsu et al., (2008) Piezoelectricity of Chiral Polymeric Fiber and Its Application in Biomedical Engineering. IEEE Transactions on Ultrasonics, Ferroelectrics, and Frequency Control, vol. 55, No. 5, pp. 1000-1008.
Ando, E. Fukada, J. Polym. Sci. Pol. Phys. 14, 63-79 (1976).
Barroca et al., "Protein adsorption on piezoelectric poly(L-lactic) acid thin films by scanning probe microscopy," Applied Physics Letters, vol. 98, Iss. 13, 133705, Mar. 2011.
Bergman, J.H. McFee, G.R. Crane, Appl. Phys. Lett. 18, 203-205 (1971).
Campagnola et al., Biophys. J. 82, 493-508 (2002).
Chang et al., J. Chem. Phys. 111, 6136-6143 (1999).
Farrar, J.E. West, I.J. Busch-Vishniac, S.M. Yu, Scripta Mater. 59, 1051-1054 (2008).
Farrar et al., Adv. Mater. 23, 3954-3958.
Fukada, Ferroelectrics 60, 285-296 (1984).
Fukada, I. Yasuda, J. Phys. Soc. Jpn. 12, 5 (1957).
Fukada, J. Phys. Soc. Jpn. 10, 149-154 (1955).
Fukada, J. Phys. Soc. Jpn. 11, 1301 (1956).
Fukada et al., J. Macromol. Sci.-Phys. B 8, 475481 (1973).
Fukuda, "Recent developments of polar piezoelectric polymers," IEEE Transactions on Dielectrics and Electrical Insulation, vol. 13, pp. 1110-1119, 2006.
Fukuto et al., J. Chem. Phys. 119, 6253-6270 (2003).
Furukawa et al., Ferroelectrics 32, 61-67 (1981).
Furukawa, IEEE T Electr. Insul. 24, 375-394 (1989).
Furukawa, K. Ogiwara, E. Fukada, J. Polym. Sci. Pol. Phys. 18, 1697-1706 (1980).
Go, S. Ejiri, E. Fukada, BBA-Protein Struct. M. 175, 454-456 (1969).
Konaga, E. Fukada, J. Polym. Sci. Pol. Phys. 9, 2023 (1971).
Kryszewski, "Fifty years of study of the piezoelectric properties of macromolecular structued biological materials," Acta Pyhsica Polonica A, vol. 105, p. 389, 2004.
Lang et al., "Review of some lesser-known applications of piezoelectric and pyroelectric polymers." Applied Physics A: Material Science and Processing 85 (2), pp. 125-134, 2006.
Murthy, E. T. Samulski, J.R. Knox, Macromolecules 19, 941-942 (1986).
Nakiri, K. Irnoto, M. Ishizuka, S. Okamoto, M. Date, Y. Uematsu, E. Fukada, Y. Tajitsu, Jpn. J. Appl. Phys. 43, 6769-6774 (2004).
Nakiri, M. Okuno, N. Maki, M. Kanasaki, Y. Morimoto, S. Okamoto, M. Ishizuka, K. Fukuda, T. Takaki, and Y. Tajitsu, Jpn. J. Appl. Phys. 44, 7119-7122 (2005).
Narniki, R. Hayakawa, Y. Wada, J. Polym. Sci. Pol. Phys. 18, 993-1004 (1980).
Neese et al., Appl. Phys. Left. 90, 3 (2007).
Ren, Y.M. Liu, H. Hofmann, Q.M. Zhang, J. Blottman, Appl. Phys. Lett. 91, 3 (2007).
Tajitsu et al., "Piezoelectric poly-L-lactic acid film prepared by a new method," Japanese Journal of Applied Physics, Part 1: Regular Papers and Short, vol. 42, pp. 6172, 2003.
Teferi et al., "Magnetoelectric coupling in multiferroic heterostructure of rf-sputtered NiMnGa thin film on PMNPT," Journal of Magnetism and Magnetic Materials, vol. 324, pp. 1882-1886, Jun. 2012.
Worley, R.W. Linton, E.T. Samulski, Langmuir 11, 3805-3810 (1995).
Yu et al., Nature 389, 167-170 (1997).
Zhang, C. Huang, F. Xia, J.Su, Eds: Y. Bar-Cohen, Electroactive Polymer (EAP) Actuators as Artificial Muscles, vol. 2, (SPIE Press, WA, USA 2004, Chapter 4).

* cited by examiner

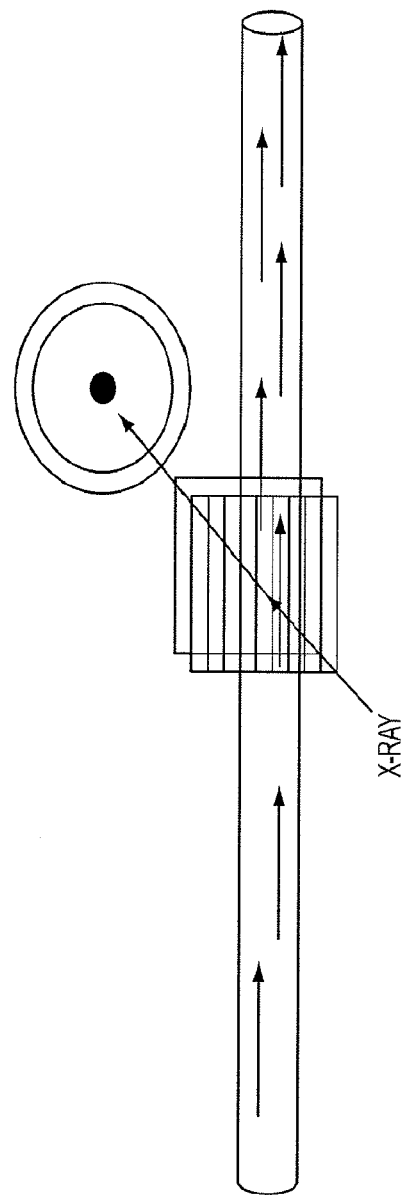
FIG. 5

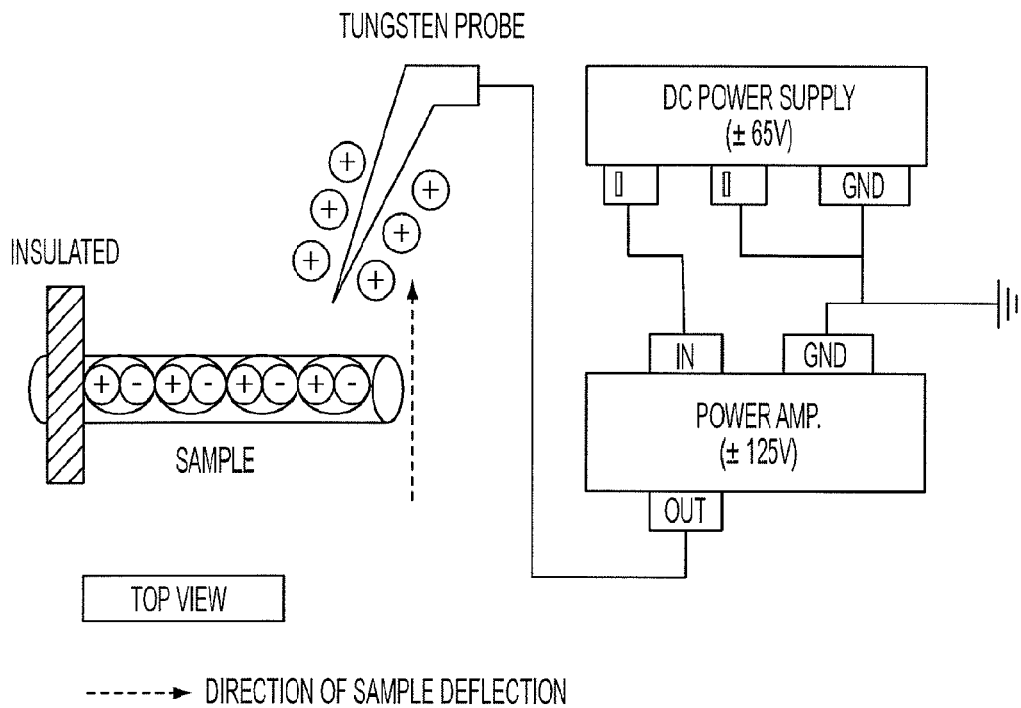
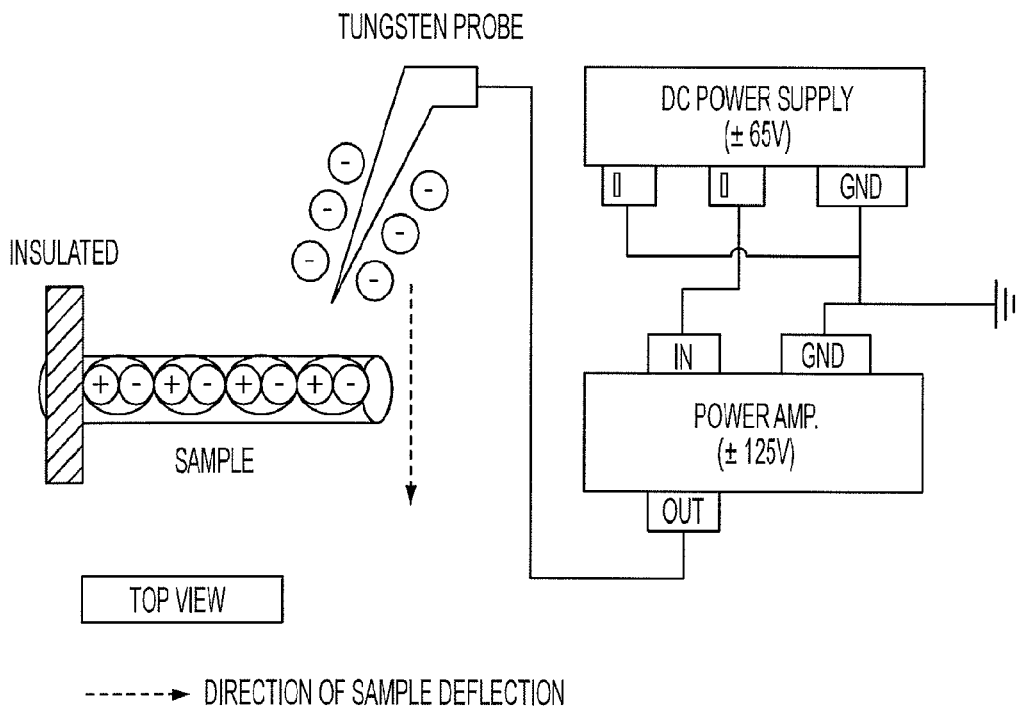
FIG. 9

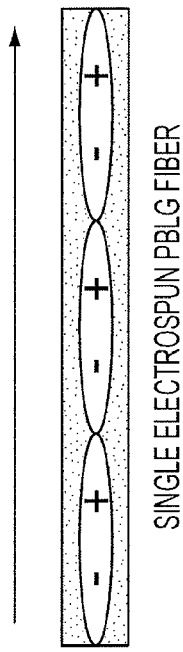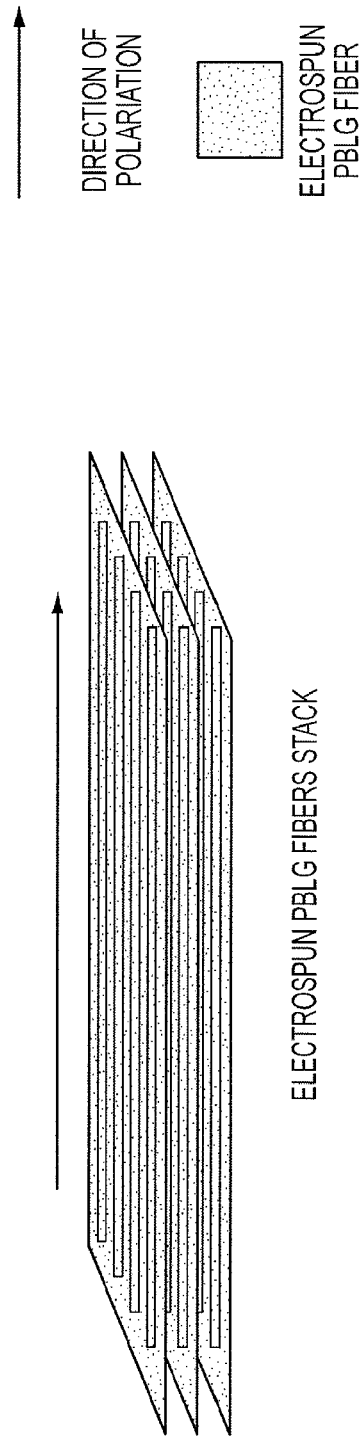
FIG. 12
FIG. 13

PIEZOELECTRIC POLYMER FIBERS

CROSS-REFERENCE TO RELATED APPLICATION

This application is a National Stage Application of International Application No. PCT/US2009/054326 filed Aug. 19, 2009, which claims priority to U.S. Provisional Application No. 61/090,060 filed Aug. 19, 2008, the entire contents of both of which are hereby incorporated by reference in their entirety.

This invention was made using U.S. Government support under Office of Naval Research award Number G040-E70-025-1000. The U.S. Government has certain rights in this invention.

BACKGROUND

1. Field of the Invention

The present invention relates to piezoelectric fibers, articles comprising piezoelectric fibers, methods for making piezoelectric fibers and electronic devices using piezoelectric fibers.

2. Background

Piezoelectricity refers to a phenomenon observed in some materials in which imposition of a stress will establish an electric field whose intensity is proportional to the stress level. This phenomenon is credited to Jacques and Pierre Curie who discovered piezoelectricity in quartz in 1880 (Curie, P. J. and J. Curie, *Crystal Physics-Development by Pressure of Polar Electricity in Hemihedral Crystals with Inclined Faces*. Acad. Sci. (Paris) C.R. Hebd Seances, 1880. 91: p. 294), but the materials most often in use today as piezoelectrics are barium titanate ($BaTiO_3$) and lead zirconate titanate (PZT). Both are ceramic materials which require high temperature processing in the presence of a high electric field in order to render them piezoelectric. They tend to be expensive and brittle materials. (See Rosen, C. Z., B. V. Hiremath, and R. E. Newnham, eds. *Piezoelectricity*. 1992, American Institute of Physics: New York for a review of piezoelectricity.)

Piezoelectric materials exhibit a linear coupling between a stress field and an electric field. Equations show that piezoelectricity works either with a mechanical field inducing an electrical one, or vice versa. Generally transduction from a mechanical signal to an electrical signal is referred to as sensing, while transduction using electrical input to produce a mechanical output is referred to as actuation. In order to fully investigate piezoelectric materials, it is necessary to consider both sensing and actuation because some measurements are easier to make on sensors and others on actuators.

$BaTiO_3$ and PZT, were first discovered in the late 1940s and early 1950s (Jaffe, B. 1955: U.S. Pat. No. 2,708,244, issued May 10, 1955; Gray, R. B. 1949: U.S. Pat. No. 2,486,560, issued Nov. 1, 1949). Efforts since then to find new piezoelectric materials generally have met with disappointment. The most promising development was the discovery of piezoelectricity in PVDF, but this polymer loses its piezoelectricity at a relatively low temperature (70° C.) and requires uniaxial or biaxial stretching in order to introduce piezoelectricity (Kawai, H., *The Piezoelectricity of Poly(vinylidene Fluoride)*. Jpn. J. Appl. Phys., 1969. 8: p. 975). Mechanical fatigue is also a problem with PVDF. Few commercial products using piezoelectric PVDF have been marketed although the military has employed thick PVDF hydrophones.

Recently, there has been work on piezoelectricity in polypropylene foam, often written as LDPP for low density polypropylene. (See Gerhard-Multhaupt, R. *Voided polymer electrets-New materials, new challenges, new chances.* in *11th International Symposium on Electrets.* 2002 for a review.) LDPP is produced in a blow-extrusion process that results in polypropylene with closed cell spherical voids. The material is then biaxially stretched to produce disk-shaped voids. It is exposed to corona charging at levels of about 20 kV that cleaves the molecular bonds of the gas trapped in the voids yielding a $d_{33}$ of up to 300 pC/N. LDPP has a couple inherent problems that will likely limit its ultimate application in transducers. First, it loses its piezoelectric function starting at about 50° C. This means that the material is inappropriate for any use that will cause significant warming (potentially any operation in air, for instance). Second, at high pressures, it is likely the relatively low stiffness of the air voids compared to the polymer will result in collapse of the voids, possibly with discharging. Thus it is not appropriate for high pressure use.

Composites formed by placing a piezoelectric material in a polymer matrix have also been pursued successfully for many years. The bulk of the work has been on 1-3 composites, in which rods of piezoelectric materials (PZT or $BaTiO_3$) are embedded in a polymer matrix. Applications of piezoelectric 1-3 composites have focused on sonar although there has been increasing interest in their use as well for nondestructive evaluation of structures and acoustic monitoring of faults in the nuclear industry (Fleury, G. and C. Gondard, *Improvements of Ultrasonic Inspections through the Use of Piezo-Composite Transducers*. Transducer Workshop, 1996). Compared to the standard piezoelectric materials, 1-3 composites are lower mass and more rugged. Volume fractions of the ceramic component vary from 0-50% with thicknesses ranging from fractions of a millimeter to 25 millimeters (Benjamin, K., *Recent Advances in 1-3 Piezoelectric Polymer Composite Transducer Technology for AUV/UUV Acoustic Imaging Applications*. J. Electroceramics, 2002. 8: p. 145). The material typically is produced using an injection molding process to produce ceramic rods in a pattern with a plate structure at one end to keep the rod spacing and alignment fixed. A polymer then fills the regions between the rods, and the plate end is sliced off.

Piezoelectric materials are the key components of electromechanical transducers (sensors and actuators) for automatic control systems, and measurement and monitoring systems. Electromechanical transducers have become ubiquitous in our world, being found in everything from hearing aids to automobiles, from clothing dryers to perimeter sensors, and from elevators to computers. The history of transduction reads like a time line for materials invention with each new coupling mechanism discovery leading to new devices (Busch-Vishniac, I. J., *Electromechanical Sensors and Actuators*. 1999, New York: Springer). The common characteristic of electromechanical sensors and actuators is that they are electrical at one end and mechanical at the other. The linking of these two energy domains occurs typically through exploitation of electromechanical coupling phenomena in materials.

The most common acoustics transducers are microphones and loudspeakers. They are found in every telephone, in tape and digital audio recorders, and increasingly in automobiles, where they are being used for hands-free communication and in monitoring engine performance. Today, most common microphones are electret microphones. Electret materials are those which exhibit a permanent polarization or space charge. First reported in 1962 (Sessler, G. M. and J. E. West, *Self-Based Condenser Microphone with High Capacitance*. J. Acoust. Soc. Am., 1962. 34: p. 1787), electret microphones use a membrane suspended under tension above a rigid backplate, a perforated backplate and back cavity to reduce stiffness, and a small hole through the structure for dc pressure equalization.

By contrast, a piezoelectric microphone can be much simpler in structure. The piezoelectric material serves as the dielectric element, with a metal surface on top and bottom. It is unnecessary to supply any tension, to vent the device, or to provide a back cavity and perforated backplate. The result is a very simple microphone in which the material is contained either in a ring allowing sound access from both sides (a gradient microphone) or in a cylinder closed at one end (conventional pressure microphone). While it is possible to make piezoelectric microphones from $BaTiO_3$ and PZT, they are generally less sensitive and more expensive than electret microphones.

SUMMARY OF THE INVENTION

An embodiment of the current invention provides piezoelectric fibers comprising a polypeptide, wherein molecules of the polypeptide have electric dipole moments that are aligned such that the piezoelectric fiber provides a piezoelectric effect.

A piezoelectric component according to an embodiment of the current invention provides a plurality of piezoelectric fibers, each comprising an organic polymer, wherein molecules of the organic polymer have electric dipole moments that are aligned such that each of the piezoelectric fibers provides a piezoelectric effect at an operating temperature. The electric dipole moments in the different fibers are non-randomly oriented.

A method of producing piezoelectric fibers according to an embodiment of the current invention includes electrospinning a polymer solution to form a fiber, and winding the fiber onto a rotating target. The rotating target is electrically grounded.

The invention further includes electronic devices using individual piezoelectric fibers, and electronic devices using a plurality of aligned piezoelectric fibers.

An acoustic sensor according to an embodiment of the current invention includes a plurality acoustic transducers, wherein the plurality of acoustic transducers are structured and arranged to detect a corresponding plurality of vector components of an acoustic signal, and at least one of the plurality of acoustic transducers comprises a piezoelectric fiber.

An energy harvesting device according to an embodiment of the current invention includes a layer of a matrix material, a plurality of piezoelectric fibers embedded in the layer of matrix material such that each of the piezoelectric fibers protrudes from a first surface of the layer of matrix material, a first electrode formed on a second surface of the layer of matrix material, and a second electrode disposed in contact with the plurality of piezoelectric fibers at extruding portions of the plurality of piezoelectric fibers. The second electrode is structured to transfer an applied mechanical energy to the plurality of piezoelectric fibers.

Further objectives and advantages, as well as the structure and function of preferred embodiments will become apparent from a consideration of the description, drawings and examples.

BRIEF DESCRIPTION OF THE DRAWINGS

FIG. 5 shows an X-ray diffraction pattern of a piezoelectric fiber according to an embodiment of the present invention.

FIG. 9 shows another example of a polarity sensor device according to the present invention.

FIG. 12 illustrates a fiber according to the present invention, where the electric dipole moments of the polypeptide molecules are aligned substantially parallel to the axis of the fiber.

FIG. 13 illustrates a stack of directionally aligned fibers according to the present invention, where the directions of polarization of individual fibers are oriented in the same direction.

DETAILED DESCRIPTION

The contents of all cited references (including literature references, issued patents, published patent applications) as cited throughout this application are hereby expressly incorporated by reference.

Some embodiments of the present invention include piezoelectric fibers comprising a polypeptide, wherein molecules of said polypeptide have electric dipole moments that are aligned such that said piezoelectric fiber provides a piezoelectric effect.

As used herein, a "fiber" is a filamentous strand comprising a plurality of polymer molecules, wherein the length of the fiber is longer than its diameter. A piezoelectric fiber is a fiber according to the above definition which exhibits piezoelectric properties.

"Piezoelectric properties" as used herein, describe the ability of the fiber to produce an electric potential in response to an applied mechanic stress, or reversely, to produce mechanical stress and/or strain in response to an applied electric potential.

Figure 1:
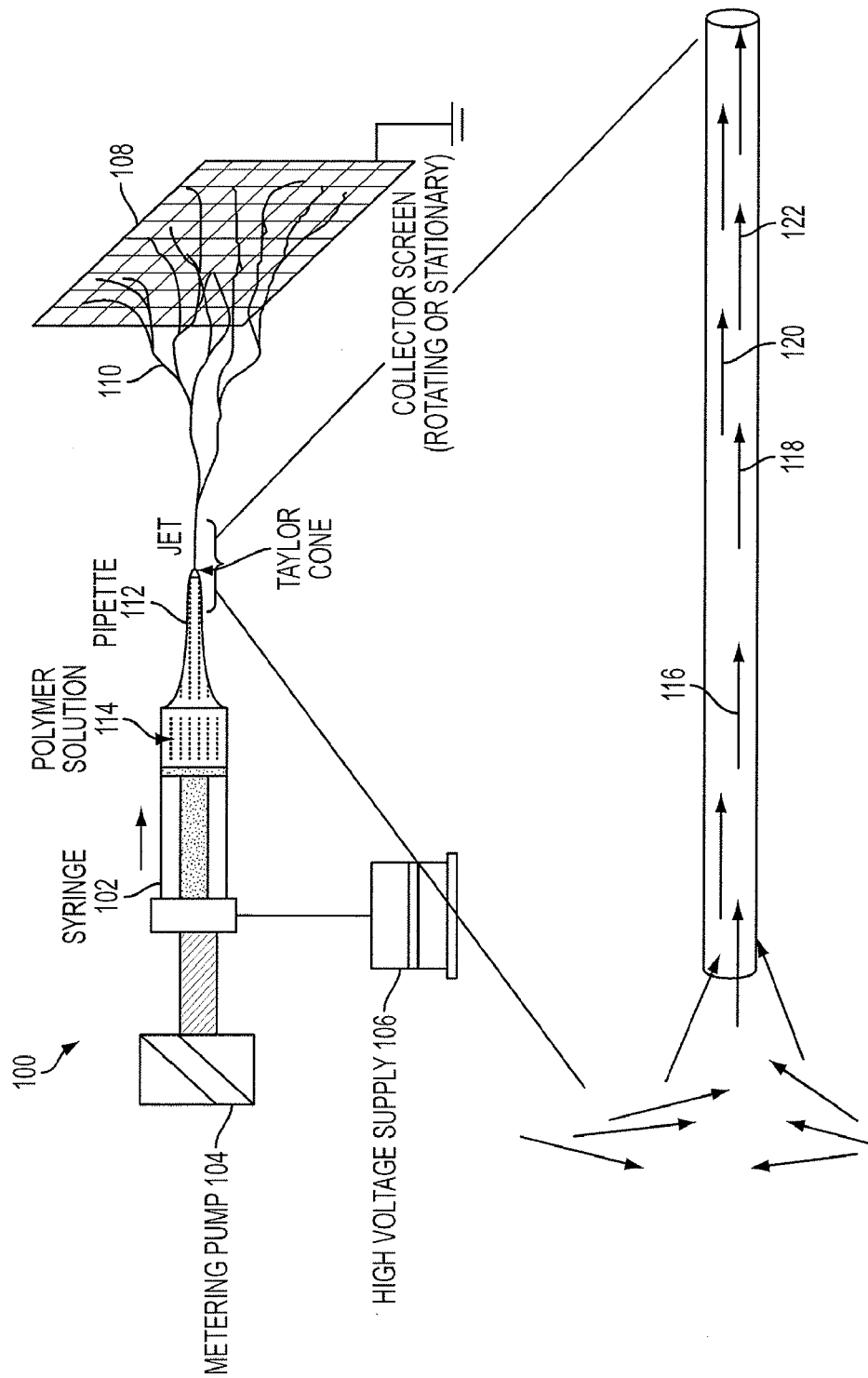
FIG. 1 is a schematic illustration of an electro-spinning process that can be used to produce fibers according to some embodiments of the current invention. A section of a fiber according to an embodiment of the current invention is illustrated schematically in FIG. 1.

FIG. 1 provides a schematic illustration of an electro-spinning system 100 that can be used to produce piezoelectric fibers according to an embodiment of the current invention. The electro-spinning system 100 includes a syringe 102, a metering pump 104, a voltage supply 106 and a collector screen 108. The voltage supply can provide high voltages up to several tens of kV in some embodiments of the current invention. For example, voltages up to 30 kV is suitable for some applications. However, some embodiments of the invention are not limited to only a maximum of 30 kV. The collector screen 108 is grounded and, in this example, stationary. With a stationary screen, the fiber 110 will typically collect in a mesh or network of randomly oriented portions of the fiber. The syringe 102 includes a pipette 112 that provides a nozzle for forming piezoelectric fibers. The syringe 102 is loaded with a polypeptide solution 114 according to some embodiments of the current invention.

A section of a piezoelectric fiber 116 is illustrated schematically in FIG. 1. Some of the polypeptide molecules that form the piezoelectric fiber 116 are represented by the arrows, such as 118, 120 and 122, for example. More particularly, the arrows, such as 118, 120 and 122, schematically represent electric dipole moments of the constituent polypeptide molecules. The direction of the arrow represents the polarity direction of the dipole moment of the polypeptide molecule. The alignment of the polypeptides is due to the direction of the applied voltage. Polarity reversal will cause the dipoles to change direction. The dipole moments of the polypeptides, such as 118, 120 and 122, are aligned in the piezoelectric fiber 116 substantially along a common direction which is the longitudinal axis of the piezoelectric fiber 116 in this case. Since the dipole moments of the polypeptides are align both in a common direction and in polarity, the piezoelectric fiber 116 exhibit a piezoelectric effect since compressing and/or stretching the piezoelectric fiber 116 produces an electric potential in response to the compressing and/or stretching. One can see that if the arrows 118 and 120, for example, were pointing in opposite directions they would tend to cancel the total dipole moment of the fiber 116 in that region. Consequently, a method of manufacturing piezoelectric fiber 116 according to the current invention seeks to provide conditions for the piezoelectric fiber 116 to substantially solidify prior to being subjected to external fields that could disrupt or randomize the polarity of the constituent polypeptide molecules so that the polarities of the constituent polypeptide molecules are predominantly aligned along a common direction. For example, if fibers are collected on a stationary collector prior to the constituent molecules within the fiber being fixed in a predominant common polarity, the polarities could be randomized, thus resulting in a fiber that does not exhibit a piezoelectric effect.

Figure 2:
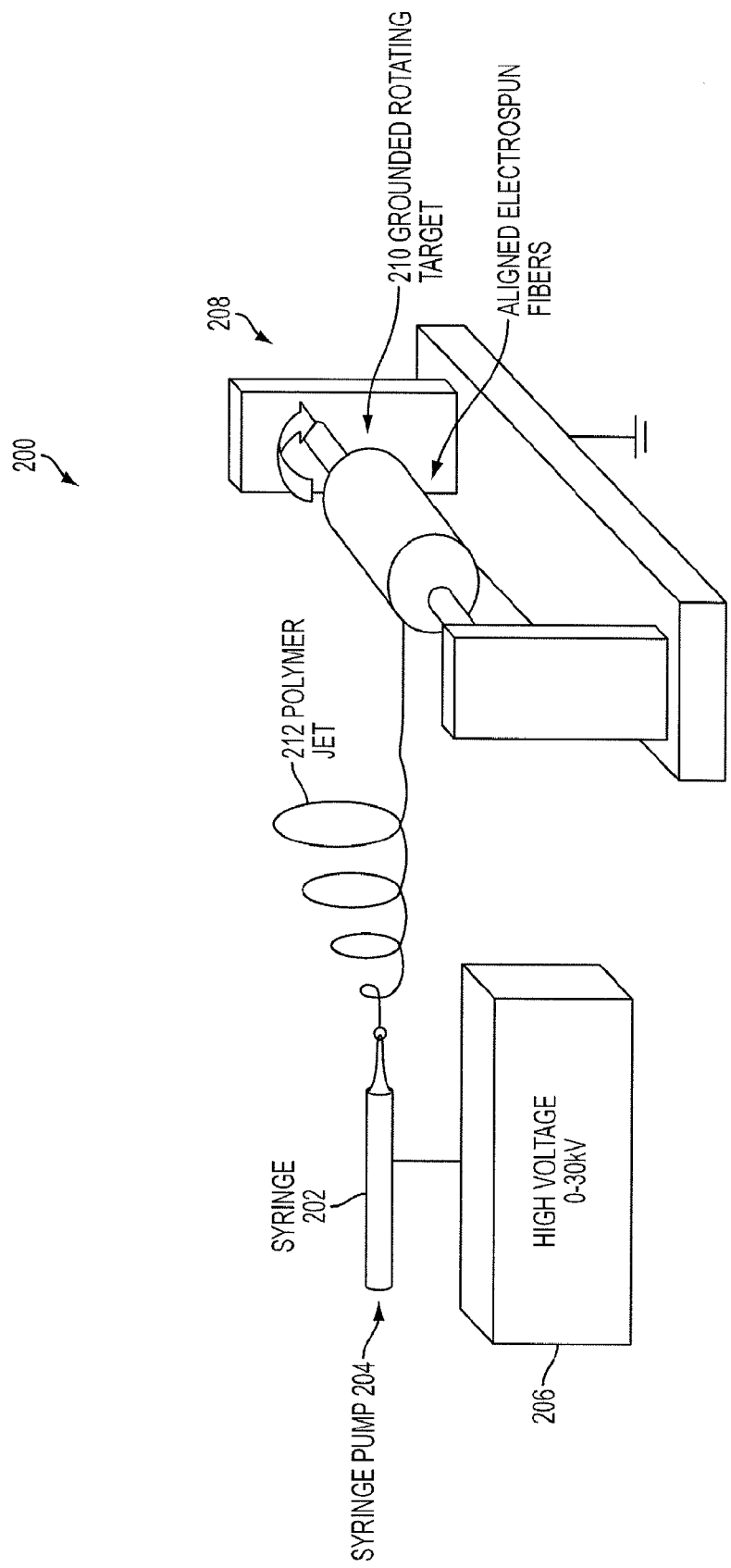
FIG. 2 is a schematic illustration of an electro-spinning apparatus according to an embodiment of the current invention that can be used to produce piezoelectric fibers according to an embodiment of the current invention.

FIG. 2 is a schematic illustration of an electro-spinning system 200 that can be used to produce piezoelectric fibers according to another embodiment of the current invention. The electro-spinning system 200 includes a syringe 202, a metering pump 204, a voltage supply 206 and a collector system 208. The collector system 208 has a grounded rotating target 210 on which piezoelectric fiber 212 can be wound as it is produced to provide long piezoelectric fibers. In this case, sections of the piezoelectric fiber 212 are substantially parallel to neighboring sections of the piezoelectric fiber 212.

Figure 4:
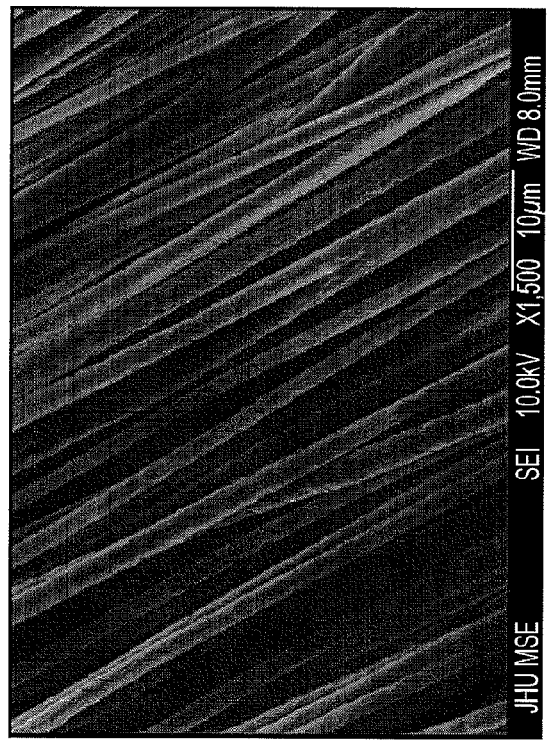
FIG. 4 shows the non-randomly oriented fibers produced by electrospinning onto a rotating target.
Figure 3:
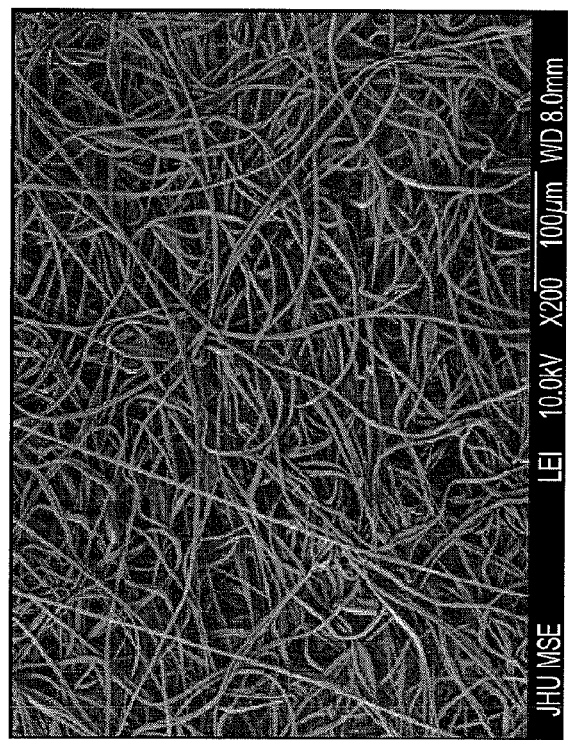
FIG. 3 shows the random orientation of fibers produced by electrospinning onto a stationary target.
Figure 6:
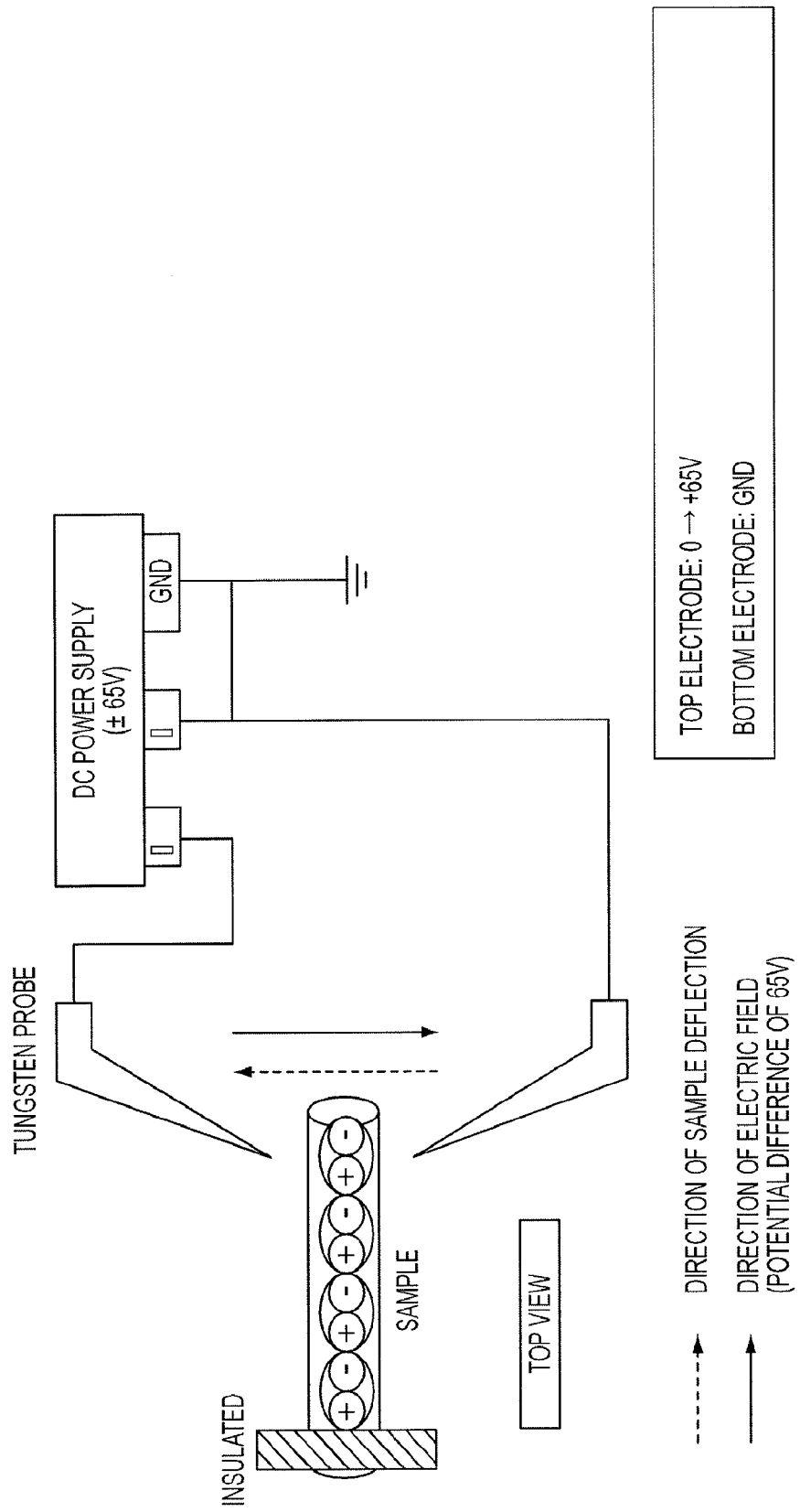
FIG. 6 shows an example of a polarity sensor device according to the present invention.
Figure 7:
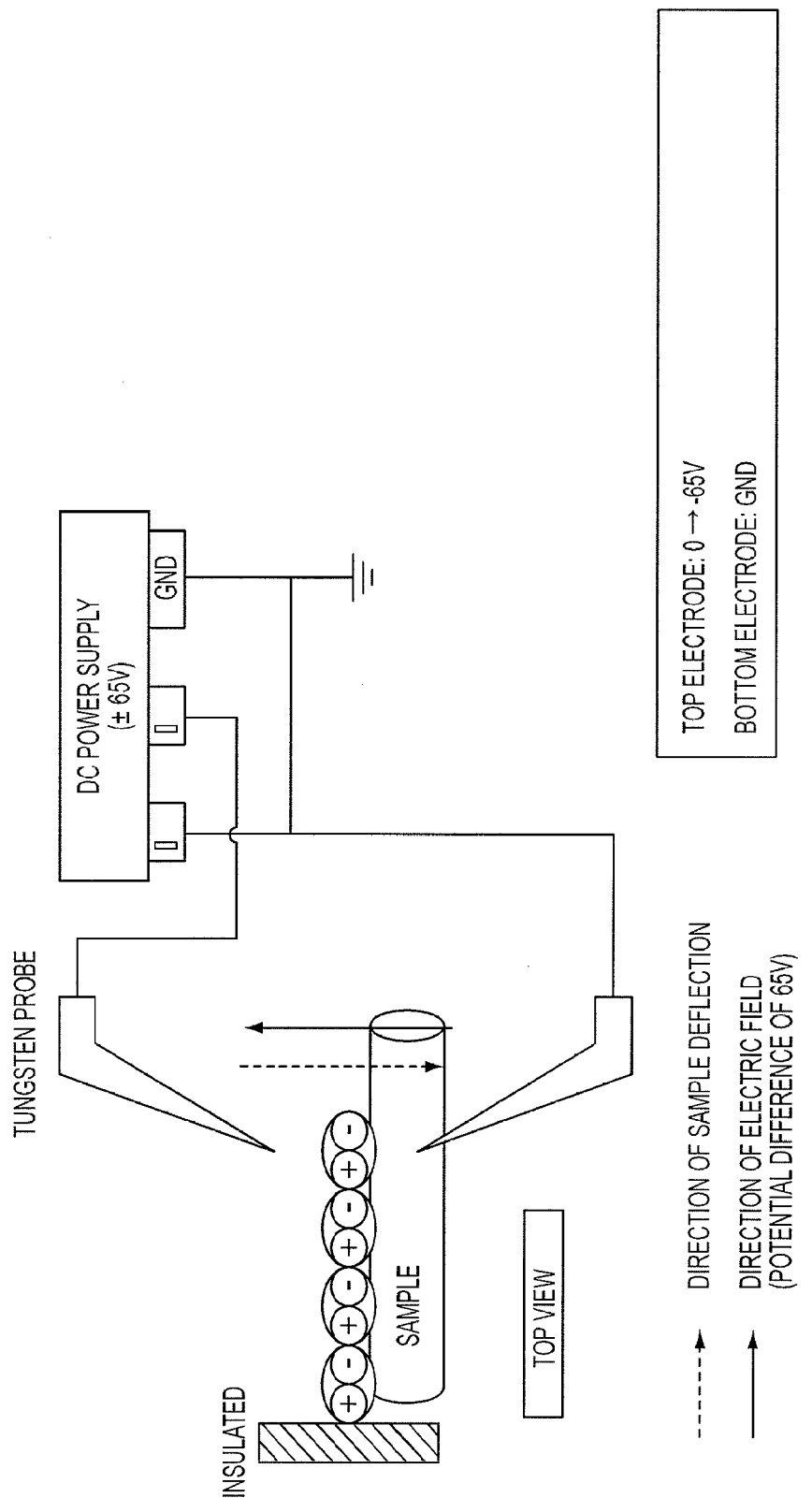
FIG. 7 shows another example of a polarity sensor device according to the present invention.
Figure 8:
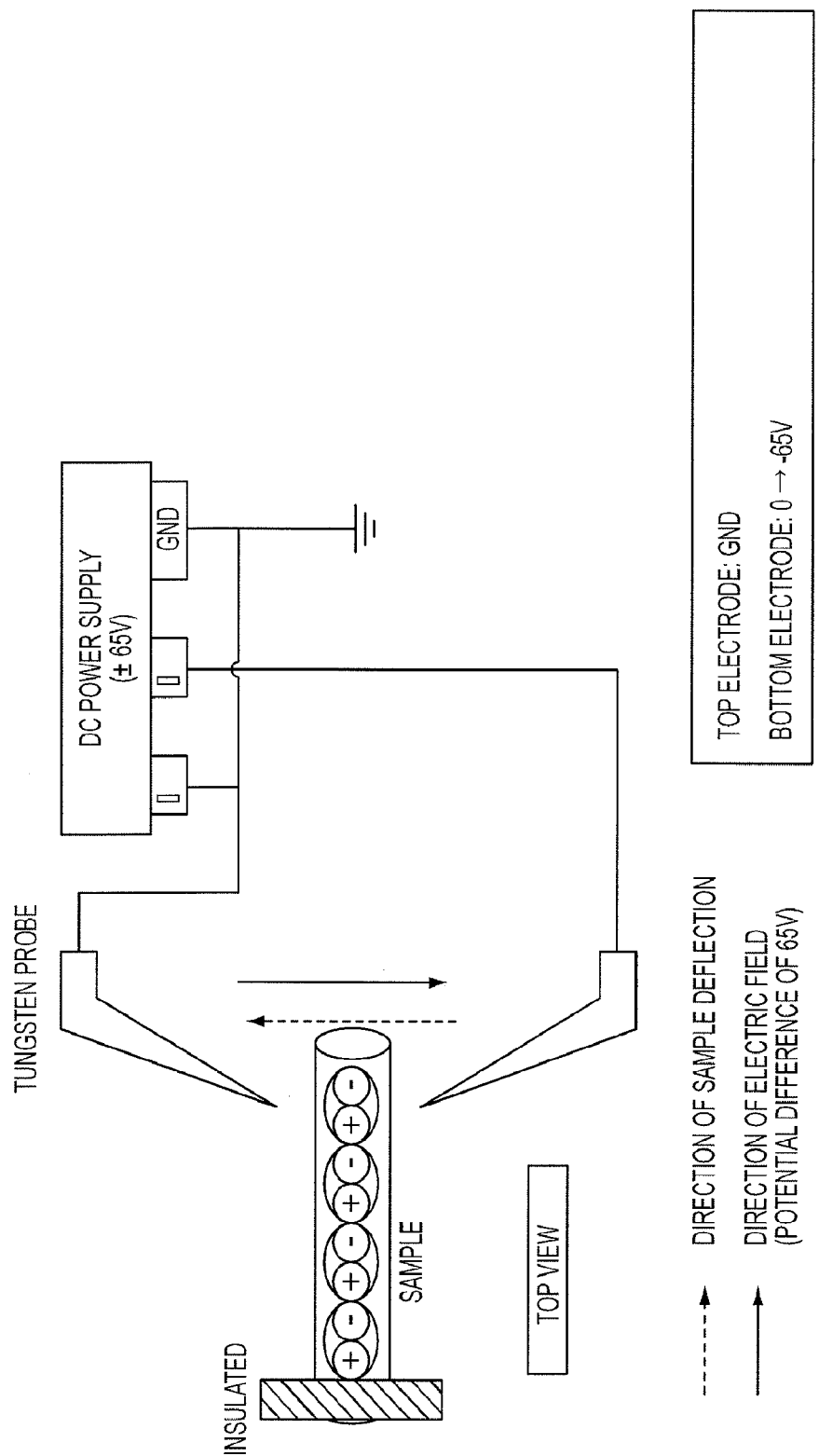
FIG. 8 shows another example of a polarity sensor device according to the present invention.

FIG. 3 shows random orientation of one or more fibers produced by an electro-spinning process such as that illustrated in FIG. 1. The fibers illustrated in FIG. 3 are piezoelectric fibers according to an embodiment of the current invention. FIG. 4 shows piezoelectric fibers produced by an electro-spinning such as illustrated in FIG. 2.

In some embodiments, the constituent polypeptide molecules have electric dipole moments greater or equal to 35 Debye. In some embodiments, the electric dipole moment of the polypeptide is between 35 and 3000 Debye. In some embodiments, the electric dipole moments of the polypeptide molecules are aligned substantially parallel to the axis of the fiber.

In some embodiments, the piezoelectric fiber can have a diameter as small as about 10 nm. In other embodiments, the diameter of the piezoelectric fiber can be as thick as about 100 µm. In some embodiments, the fiber may be between 100 nm and 50 µm in diameter. In other embodiments, the fiber has a length of at least about 200 nm. In some embodiments, the fiber can be up to 1 mm or more, up to 1 cm or more, or even several meters long. Other embodiments can include combinations of these dimensions and/or other values within the ranges depending on the particular applications. A range of diameters are useful for different applications. For example, for very small actuators very thin fibers have an advantage, on the other hand, for large actuators, thicker fibers are desirable. The diameter and length of the fiber depend on the peptide, the applied, field (voltage) and the solvent used.

In some embodiments, the piezoelectric fiber has values for the piezoelectric constants $d_{31}$ and/or $d_{33}$ of at least 1 pC/N. The piezoelectric fiber may have only one of $d_{31}$ or $d_{33}$, or may have both values. In other embodiments, the $d_{31}$ value may be between 10 pC/N and 100 pC/N. In other embodiments, the $d_{33}$ value may be between 10 pC/N to 200 pC/N. In other embodiments, the piezoelectric fibers have both $d_{31}$ and $d_{33}$ values (see descriptions e.g. in U.S. Pat. Nos. 7,101,491 and 7,045,075 regarding ceramic piezoelectric materials and their characterizations).

In certain embodiments, the piezoelectric fiber has an operating temperature at or below 60° C. In other embodiments, the operating temperature of the piezoelectric fiber can be between 4 and 80° C., 4 and 100° C., or 4 and 120° C. In other embodiments, the operating temperature of the piezoelectric fiber can be between 4 and 60° C. Piezoelectric fibers according to some embodiments of the current invention, exhibit piezoelectric properties at temperatures within this range. In other embodiments, the piezoelectric property of the fiber is stable up to a temperature of 80° C., 100° C., or 120° C. In these embodiments, the fiber exhibits a piezoelectric property at temperatures below 120° C.

In certain embodiments, the polypeptide has a helical structure. In some specific embodiments, the helical structure is an α-helical structure. A helical or α-helical structure stabilizes the secondary structure of the polypeptide, and increases the dipole moment of the polymer material. A rod-like structure of the α-helix results in a unique set of properties including a large anisotropy and high persistence length. Polypeptides containing certain natural and synthetic amino acids spontaneously form helical or α-helical structures. For instance, polymers formed from repeating units of γ-esters of glutamic acid, β-esters of aspartic acid, alanine, phenylalanine, or combinations thereof will often form α-helical structures. Other amino acids may be used in the polypeptide, so long as the polypeptide has an overall electric dipole moment or an α-helical structure. In general, if circular dichroism (CD) indicates that the polypeptide is not a random coil, the polypeptide can be expected to have an electrical dipole moment. Whether a polypeptide forms an α-helical structure can be readily determined using standard techniques in the art. For example, infrared (IR) analysis or X-ray diffraction may confirm the presence of an α-helical structure in a polypeptide. Another technique for determining the presence of an α-helical structure in a polypeptide includes circular dichroism.

In certain embodiments, the polymer contains repeat units of γ-benzyl-L-glutamate. It has been reported that each repeat unit contributes approximately 3.5 Debye to the total helix dipole.

In certain embodiments, the polypeptide has a degree of polymerization of at least about 20 up to about 3000. In other embodiments, the degree of polymerization of the polypeptide is between 100 and 2000.

As used herein, "γ-esters of glutamic acid" have the structure of glutamic acid, with an ester at the γ-carboxylate. As used herein, "β-esters of aspartic acid" have the structure of aspartic acid, with an ester at the p-carboxylate. The ester may be an alkyl ester, aralkyl ester, alkenyl ester, alkynyl ester, aryl ester, heteroaryl ester, or heteroarylalkyl ester. In certain embodiments, the ester is an alkyl ester or arylalkyl ester. In some embodiments, the ester is a benzyl ester.

The term "alkyl" as used herein means straight-chain, branched or cyclic $C_1$-$C_{12}$ hydrocarbons which are completely saturated and hybrids thereof such as (cycloalkyl) alkyl. The terms "alkenyl" and "alkynyl" used alone or as part of a larger moiety include both straight and branched chains containing two to twelve carbon atoms. The term "cycloalkyl" used alone or as part of a larger moiety include cyclic $C_3$-$C_{12}$ hydrocarbons which are completely saturated or which contain one or more units of unsaturation, but which are not aromatic.

The term "aryl" used alone or as part of a larger moiety as in "aralkyl", refers to mono-, bi-, or tricyclic aromatic hydrocarbon ring systems having five to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl or tetrahydronaphthyl, where the radical or point of attachment is on the aromatic ring. The term "aralkyl" refers to an alkyl group substituted by an aryl. Examples of aralkyl groups include, but are not limited to, benzyl and phenethyl.

The term "heteroaryl", used alone or as part of a larger moiety as in "heteroaralkyl", refers to heteroaromatic ring groups having five to fourteen members, preferably five to ten, in which one or more ring carbons, preferably one to four, are each replaced by a heteroatom such as N, O, or S. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroaromatic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic". The term "heteroaralkyl" refers to an alkyl group substituted by a heteroaryl.

An aryl (including the aryl moiety in aralkyl) or heteroaryl (including the heteroaryl moiety in heteroaralkyl) group may contain one or more substituents. Examples of suitable substituents on the unsaturated carbon atom of an aryl or heteroaryl group include a halogen, —R*, —OR*, —SR*, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO$_2$, —CN, —N(R*)$_2$, —NR*C(O)R*, —NR*C(O)N(R*)$_2$, —NR*CO$_2$R*, —NR*NR*C(O)R*, —NR*NR*C(O)N(R*)$_2$, —NR*NR*CO$_2$R*, —C(O)C(O)R*, —C(O)CH$_2$C(O)R*, —CO$_2$R*, —C(O)R*, —C(O)N(R*)$_2$, OC(O)N(R*)$_2$, —S(O)$_2$R*, —SO$_2$N(R*)$_2$, —S(O)R*, —NR*SO$_2$N(R*)$_2$, —NR*SO$_2$R*, —C(S)N(R*)$_2$, —C(NH)N(R*)$_2$, wherein each R* is independently selected from hydrogen, a substituted or unsubstituted alkyl, alkenyl, OR alkynyl group, an unsubstituted heteroaryl or heterocyclic ring, phenyl (Ph), substituted Ph, —O(Ph), substituted —O(Ph), —CH.sub.2 (Ph), or substituted —CH.sub.2(Ph); y is 0-6; and Y is a linker group. Examples of substituents on the aliphatic group or the phenyl ring of R* include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

The polypeptides of the present invention may be prepared by methods known in the art. For example, the polymers may be prepared by ring-opening polymerization of an N-carboxyanhydride (NCA) precursor, initiated by a base or organometallic (zerovalent nickel) reagent as described by Deming et al. (*Facile synthesis of block copolypeptides of defined architecture*. Nature, 1997. 390: p. 386-389), and illustrated in the scheme below, where R is the side-chain of the amino acid and n is the degree of polymerization.

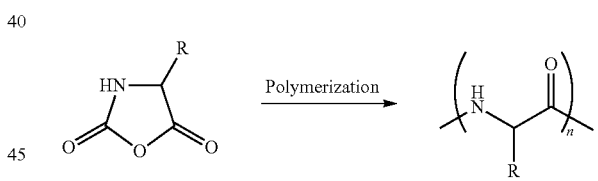

In some embodiments, the piezoelectric fiber includes a polypeptide other than poly(γ-benzyl-L-glutamate).

Further embodiments of the current invention include methods of producing piezoelectric fibers comprising electrospinning a solution of a polypeptide into a fiber. The molecules of the polypeptide have electric dipole moments that are aligned such that the piezoelectric fiber provides a piezoelectric effect at an operating temperature. Such polypeptides may be any of the polypeptides described previously.

Further embodiments of the current invention include methods of producing piezoelectric fibers comprising electrospinning a polymer solution onto a rotating target. In some embodiments, the target rotates around an axis perpendicular to the direction of the polymer solution stream to roll the piezoelectric fiber onto a spool. In some embodiments, the target is grounded and a voltage is applied to the polymer solution. In some embodiments, the voltage is at least 1 kV. The voltage level depends on the polypeptide and other material parameters. In some embodiments, the voltage is greater than 10 kV. For example, for high molecular weight polypeptides, an increased voltage may be necessary. In some embodiments, the target rotates at a rate of at least 100 rotations per minute (rpm). The rotation speed also depends on the polypeptide and other material parameters. For example, a particular polypeptide may require a faster or slower rotation speed, depending on the specific polypeptide, molecular weight or other parameters.

Electrospinning includes spinning polymer solutions or melts in high electric fields. A schematic of the electrospinning process is shown in FIG. 1. The process is based on the principle that strong electrical forces overcome weaker forces of surface tension in the charged polymer liquid. At certain threshold voltage, a fine charged jet is ejected from the tip of a capillary tube. Subsequently, the jet moves in the direction of the ground plane or opposite voltage potential to the applied electric field and elongates according to external and internal electrical forces.

One possible explanation for how electrospinning produces the fibers such that the electric dipole moments of the polymers are directionally aligned parallel to the fiber axis is based on the hypothesis that the strong electrical field that the polymer is subjected to by the electrospinning condition, in conjunction with the shear force induced by the spinning process, would pole the polymer molecules along the length of the fiber. This creates fibers with electric dipoles directionally aligned parallel to the fiber axis as shown in FIG. 1.

Electrospinning a polymer onto a rotating target as illustrated in FIG. 2 produces fiber strands where the electric dipoles of individual fiber strands are aligned in a non-random fashion. For example, fibers of poly(γ-benzyl-L-glutamate) are random when the substrate is stationary (FIG. 3), and aligned when the substrate rotates (FIG. 4). Studies involving x-ray diffraction (FIG. 5) and polarity measurements (FIG. 6-9) indicate that the electric dipoles of individual PBLG molecules are oriented along the fiber axis and that the fibers posses electroactivity.

Other embodiments of the current invention are directed to devices that include one and/or more piezoelectric fibers according to the current invention. In these embodiments, the piezoelectric fibers may be any of those discussed previously, and may or may not include poly-L-lactic acid and poly(γ-benzyl-L-glutamate) fibers.

In some embodiments, the devices may further comprise a matrix polymer. The matrix polymer is a non-piezoelectric material which provides structural and mechanical support for the piezoelectric fiber. The matrix polymer may be, for example, an organic or silicon-based polymer. In certain embodiments, the matrix polymer is selected from methylmethacrylate (MMA), poly(methylmethacrylate) (PMMA), polyethylene, polyvinylchloride, or poly(1-butene). In other embodiments, the matrix polymer is a silicone elastomer or silicone rubber. In other embodiments, the matrix polymer may be a derivative of poly(acrylate) such as poly(butylacrylate) and copolymers thereof. In certain embodiments, the piezoelectric fibers may be fully encased in the matrix, while in other embodiments, the fibers may extrude from the one or more surfaces or edges of the matrix. In other embodiments, one or more edges may be in contact with an electrode or other layer.

In certain embodiments, one or more piezoelectric fibers may be incorporated into a film. The films may be flat, shaped, or molded. In certain embodiments, the films may be flexible. In certain embodiments, the piezoelectric fibers are oriented parallel to the surface of the film. In other embodiments, the piezoelectric fibers are oriented perpendicular to the surface of the film. In certain embodiments, one more surfaces or edges of the film may be in contact with an electrode or other layer. The thickness of such a film ranges from about 5 μm to about 500 μm in some embodiments of the current invention. In some embodiments, the film has a thickness ranging from about 25 μm to about 100 μm.

In some embodiments, the electronic devices use single fibers. Examples of single fiber devices include, but are not limited to, nanoswitches or microswitches. Examples of nanoswitches can have the same or similar structure as the polarity detectors illustrated in FIG. 6-9. In these devices a single piezoelectric fiber or small bundle of fibers are placed between two electrodes or in proximity to a charged probe (FIG. 9). The motion of the piezoelectric fiber indicates the polarity of the probe, depending on whether the fiber moves towards the probe, or away from the probe. Consequently, these can be used as a switch to close a contact. Forming a switch requires metallic tips on the fiber.

In other embodiments, single piezoelectric fibers or small bundles can be used as proximity sensors, where the fiber is used to detect boundaries in the same manner as a cat's whiskers. In such embodiments, the fiber would produce an electrical signal when brushed against an object or obstacle, or to determine when two objects are in close proximity.

In other embodiments, a single piezoelectric fiber may be wrapped around a flexible tube. In some specific embodiments the flexible tube is nanosized. When a voltage is applied to the fiber, the diameter of the tube is changed. In such cases, the piezoelectric fibers can be used to control flow rate through the tube, even to the point of squeezing the tube shut, and thus preventing flow through the tube. Such a structure can provide a valve.

Other embodiments include the use of one of more fibers in a cantilever configuration, similar to the switch configurations of FIG. 6-9. Such cantilevers may be monomorph or bimorph, and can be used in a variety of applications including transducers, sensors, acutators, and energy harvesting devices. For example, monomorph and bimorph sensors are useful for the activation of microphones, phonograph stylus and in some accelerators.

Other embodiments include devices comprising a plurality of aligned fibers embedded in a matrix to form a film. In certain embodiments, the aligned fibers may be embedded in silicone rubber or other elastic matrix. In certain embodiments, the fibers are oriented parallel to the surface of the matrix, with an electrical connection to the fiber. In such devices, when the elastic matrix is stretched or compressed a voltage is generated. Such an arrangement can be used, for example, in large area transducers for both transmission and reception of sound. In other embodiments, the fibers may be cut into short aligned pieces, and embedded in a matrix perpendicular to the surface of the matrix to produce a flat sheet. When a weight is placed on the sheet, the device produces a signal relative to the amount of weight. Such a sheet can be used in an acoustic sensor or source (microphone or speaker, for example). This can permit simplified construction of sensor or speaker arrays, for example. In some embodiments, these can be phased arrays.

In some embodiments, the films described herein may be used alone, or may be used in combination with other piezoelectric films. Examples of other piezoelectric films are described by Yu et al. (see PCT/US2007/017725, publication number WO 2008/021191, by the same assignee as the current application, the entire content of which is incorporated herein by reference).

Other embodiments include transducers produced from a plurality of aligned piezoelectric fibers embedded in a matrix. In some embodiments, large-scale transducers can be produced when the fibers are embedded in polymers with impedance close to that of air for the manufacture of large-scale transducers. In other embodiments, when one or more surfaces are metalized, the transducers may be used to transmit sound, for instance in microphones or speakers. Because piezoelectric microphones do not require external application of a bias voltage, they are particularly well suited for low power and low mass applications. With the high flexibility of the films of the present invention actuators or speakers may be manufactured which can be rolled up for storage or transport, and taped to a solid wall for rapid deployment.

In other embodiments, one or more surfaces of the matrix may be metalized in discrete regions to produce sensor arrays, where each discrete region functions as a separate sensor. In other embodiments, the matrix, including the aligned fibers may be transparent. In such applications, the matrix including the piezoelectric fibers may be used to manufacture video screens which also function as speakers for display devices such as televisions.

Since the films may be produced in large areas, they may also be used as coatings for submarines, for example. In a passive mode, such a coating would match the submarine acoustic impedance much more closely to that of sea water. In an active mode, such coatings could produce a motion designed to reduce the reflection from a sonar ping or to return a ping indicating a spurious submarine location.

Figure 10:
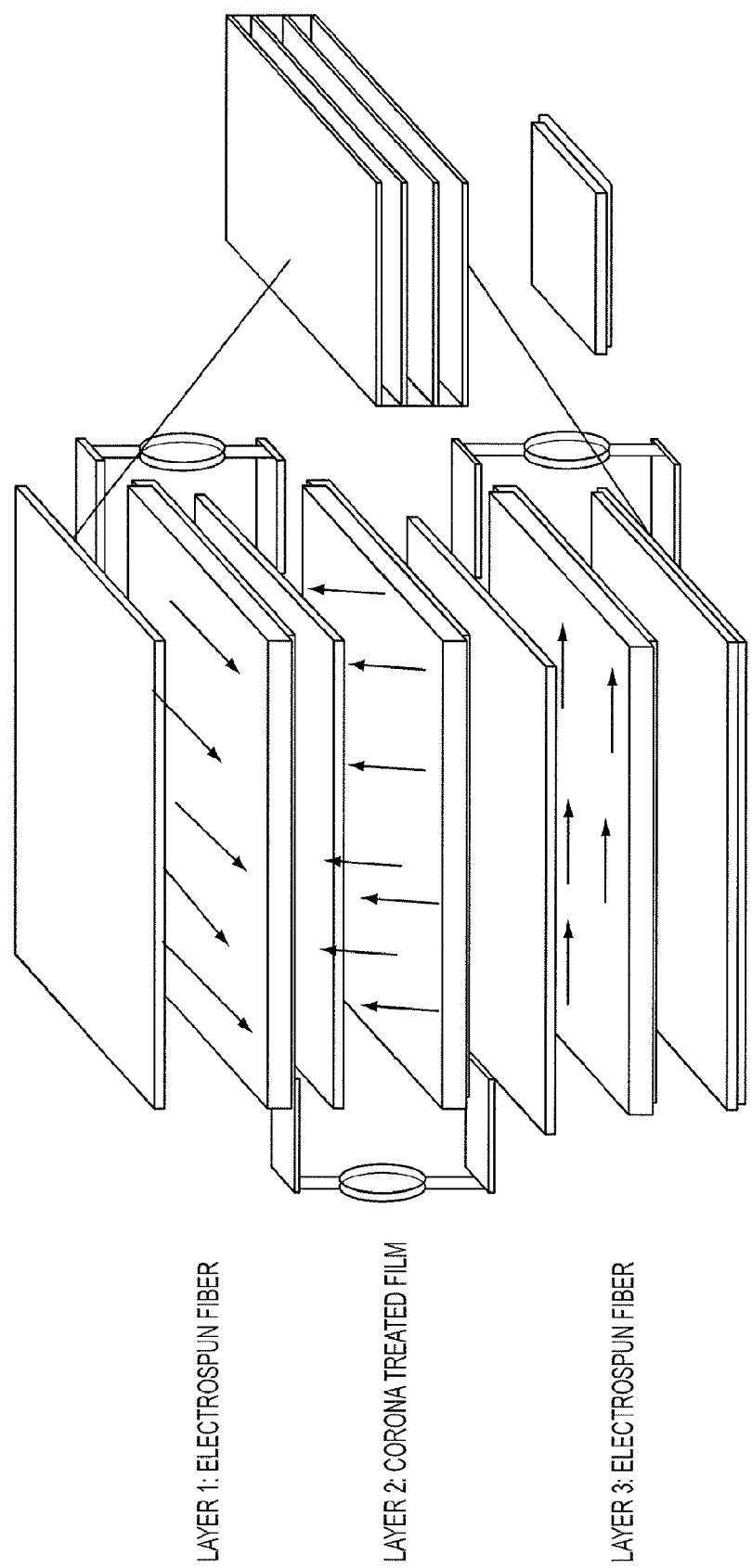
FIG. 10 shows an example of a vector sensor according to an embodiment of the present invention.

Some embodiments include vector sensors comprising a plurality of piezoelectric films in a stack, which are poled in orthogonal directions, wherein at least one film comprises a piezoelectric fiber or piezoelectric fiber composition discussed above. In these devices, each film is provided with a signal collection ability. A diagram of an example of a vector sensor, having three orthogonally aligned films is shown in FIG. 10. In this example, three orthogonally oriented films are provided. The first and third films include piezoelectric fibers oriented parallel to the surface of the film. The second film includes piezoelectric polymers which are oriented perpendicular to the surface of the film by corona poling, as described by Yu et al. in WO 2008/021191, which is incorporated by reference in its entirety. The second film may also include aligned fibers according to the present invention, wherein the fibers are aligned perpendicular to the surface of the film. Vector sensors may be used to determine the direction of a sound source by measuring the three vector components of the signal independently. Such devices are particularly suited for use underwater according to some embodiments of the current invention.

Figure 11:
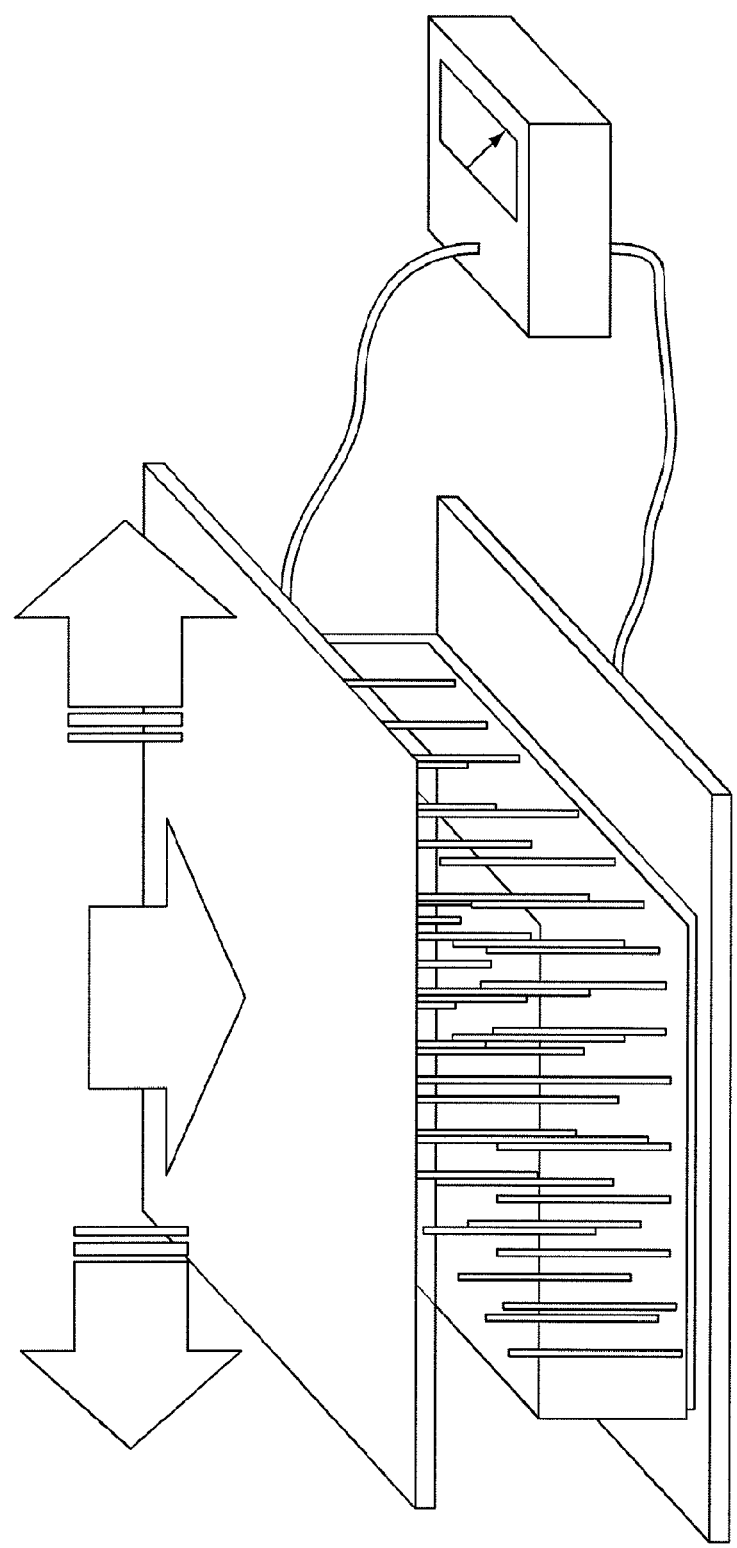
FIG. 11 shows an example of an energy harvesting device according to an embodiment of the present invention.

Other embodiments of the current invention include energy harvesting devices. An example of an energy harvesting device according to an embodiment of the current invention is illustrated schematically in FIG. 11. This embodiment of an energy harvesting device comprises aligned piezoelectric fibers embedded in a matrix to form a film with piezoelectric fibers protruding out of the top surface of the film similar to the cilia on the sensory hair cells in the ear. The matrix may be elastic (such as rubber or other elastic polymer). The bottom side of the film includes an electrode, which may also be flexible. The material of the electrode can be an electrically conductive polymer composition such as Metal Rubber™, produced by NanoSonic, Inc. In some embodiments of the current invention. However, the invention is not limited to the particular materials of the electrodes. Other materials may be suitable for other applications. On the top side of the film is a metallic surface with undulating topology in contact with the protruding fibers forming a second electrode. Movement of the top electrode due to a sonic wave or mechanical vibration induces a current in the external device. Energy converted from mechanical to electrical form can be collected, stored, or used to power small electronic devices.

The invention and the manner and process of making and using it, are described in such full, clear, concise and exact terms as to enable any person skilled in the art to which it pertains, to make and use the same.

It is to be understood that the foregoing describes some embodiments of the present invention and that modifications may be made therein without departing from the spirit or scope of the present invention as set forth in the appended claims.

EXAMPLES

Example 1

Preparation of Piezoelectric Fibers

An electrospinning apparatus is used to prepare the piezoelectric fibers as shown in (FIG. 2). PBLG (DP=760) is dissolved in dichloromethane to a concentration of 8-10% and the resulting solution is transferred to a syringe. After applying a voltage of 15 kV (using the power supply), the solution is slowly forced out of the needle of syringe at a rate of 2 mL/hr (±0.5 mL/hr depending on concentration) by pushing the plunger. The solution is jetted toward the target. During the flight, the solvent evaporates and solid fibers where the dipole moments of the PBLG are aligned (FIG. 12) are collected at the substrate. When a stationary substrate is used, fibers are randomly oriented on the collecting screen (FIG. 3) but when a rotating target is used at 2500 rpm, all fibers organize parallel to each other (FIG. 4).

Example 2

X-Ray Diffraction

The fibers produced in Example 1 were analyzed by X-ray diffraction. The X-ray diffraction (FIG. 5) showed that the PBLG molecules were oriented parallel to the fiber axis, and that the α-helical structure was preserved in the fiber.

Example 3

Piezoelectric Activity—Polarity Determination

The piezoelectrical activity of the fibers were analyzed by an apparatus composed of a DC power supply and power amp, positioning stage and micro-manipulator, tungsten probe station and microscope system, all installed on a anti-vibration table inside a temperature and humidity controlled chamber. An illustration of the testing apparatus is shown in FIG. 6-9. Piezoelectrical activity of the fiber produced in Example 1 was confirmed by exposure of the fiber to an electric field, and visual confirmation of the movement of the fiber in response to the electric field.

Example 4

Piezoelectric Activity

Figure 14:
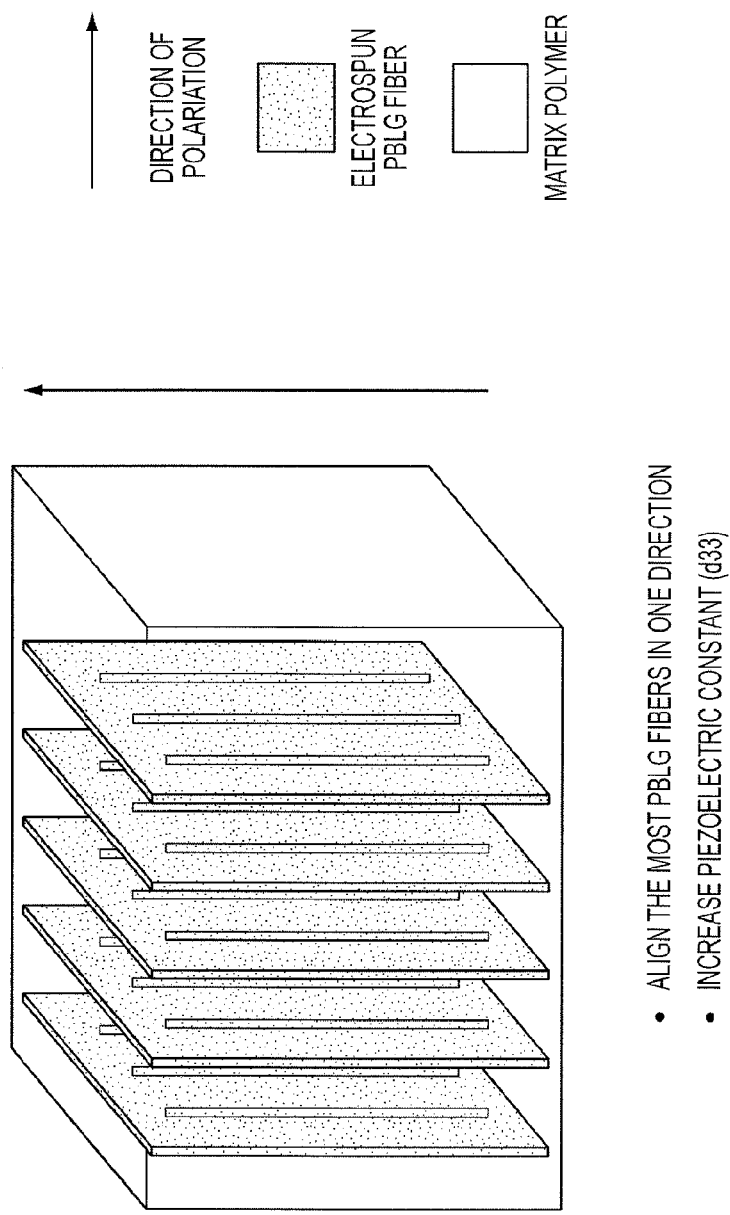
FIG. 14 illustrates a stack of directionally aligned fibers embedded in a matrix polymer.
Figure 15:
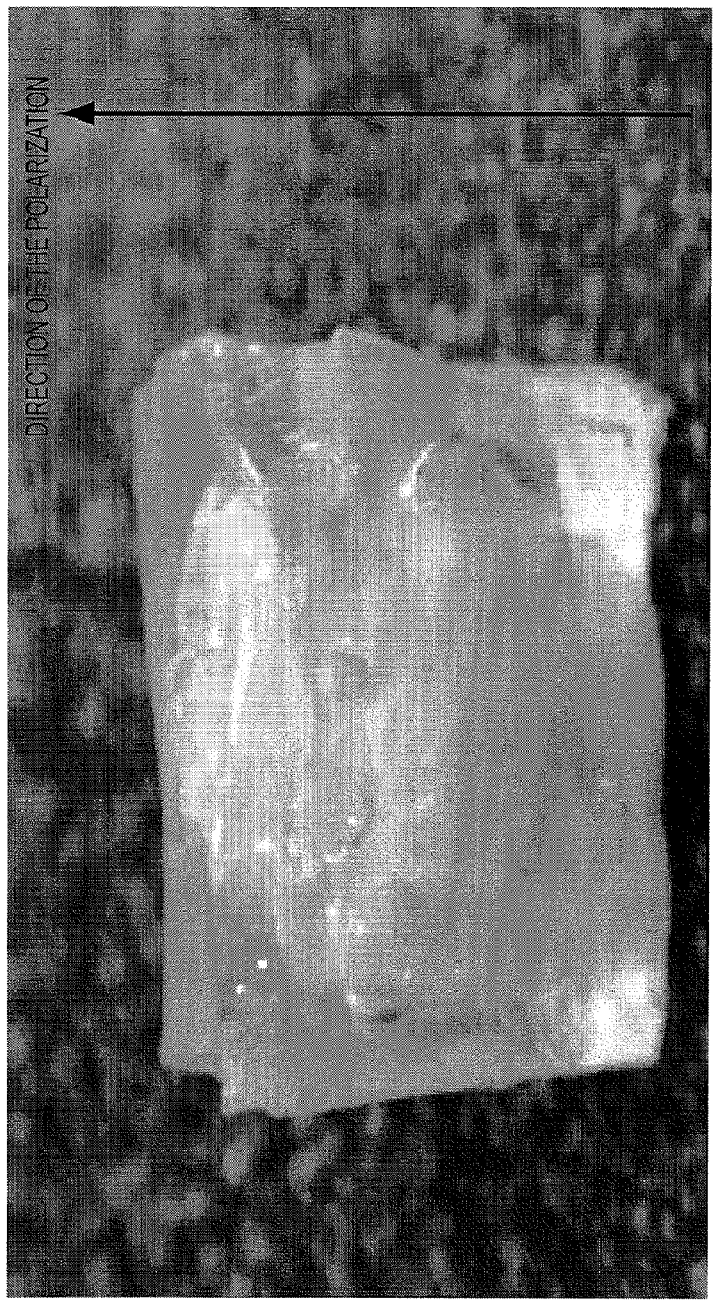
FIG. 15 shows a photograph of an embodiment where directionally aligned fibers are embedded in a silicone elastomer.
Figure 16:
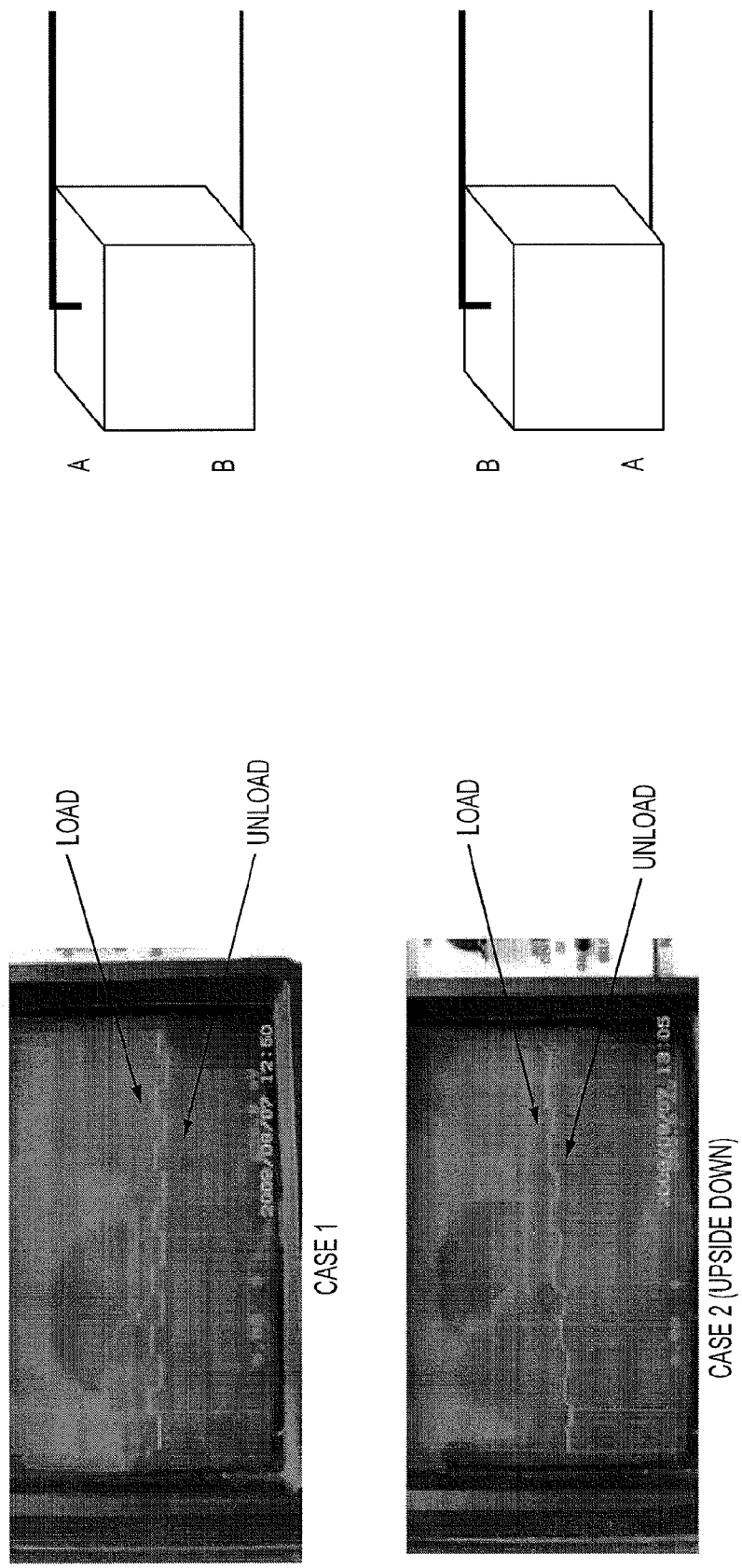
FIG. 16 shows the measurement of piezoelectric activity for one embodiment of the invention.

Piezoelectric activity of a film comprising fibers produced according to Example 1 was confirmed by embedding the fibers in silicone rubber. Parallel aligned fibers were cut into 2 cm by 2 cm pieces and stacked, keeping the direction of polarization the same for each layer of the stack (FIG. 13). The stack of parallel aligned fibers was embedded in silicone rubber, as shown in FIG. 14-15. The stack was subjected to a load of 230 g, in two orientations, as shown in FIG. 16. Case 1 produced a charge difference between −169 pC (unloaded) and −100 pC (loaded), while case 2 produced a charge difference between 308 pC (unloaded) and 243 pC (loaded). The $d_{33}$ piezoelectric value was calculated at 31 pC/N.

The invention claimed is:

1. A piezoelectric fiber comprising a polypeptide, wherein molecules of said polypeptide have electric dipole moments that are aligned such that said piezoelectric fiber provides a piezoelectric effect.

2. The piezoelectric fiber of claim 1, comprising a polypeptide other than poly(γ-benzyl-l-glutamate).

3. The piezoelectric fiber of claim 1, wherein the polypeptide molecules have electric dipole moments greater than or equal to 35 Debye.

4. The piezoelectric fiber of claim 1, wherein the electric dipole moments are aligned parallel to the axis of the fiber.

5. The piezoelectric fiber of claim 1, wherein the piezoelectric fiber has a diameter of at least 10 nm.

6. The piezoelectric fiber of claim 1, wherein the piezoelectric fiber has at least one piezoelectric constant $d_{31}$ and $d_{33}$ that is at least 1pC/N.

7. The piezoelectric fiber of claim 1, wherein the piezoelectric fiber has an operating temperature in the range of about 4° C. to 80° C.

8. The piezoelectric fiber of claim 1, wherein said polypeptide has a helical structure.

9. The piezoelectric fiber of claim 8, wherein the helical structure is an α-helix.

10. The piezoelectric fiber of claim 1, wherein said polypeptide has a degree of polymerization between about 20 and about 3000.

11. The piezoelectric fiber of claim 1, wherein the polypeptide comprises repeating residues of γ-esters of glutamic acid, β-esters of aspartic acid, alanine, phenylalanine, or combinations thereof.

12. The piezoelectric fiber of claim 11, wherein the polypeptide comprises repeating residues of γ-benzyl glutamic acid.

13. A piezoelectric component comprising a plurality of piezoelectric fibers each comprising an organic polymer wherein molecules of said organic polymer have electric dipole moments that are aligned such that each said piezoelectric fiber provides a piezoelectric effect at an operating temperature and wherein the electric dipole moments in different fibers are non-randomly oriented.

14. A piezoelectric component according to claim 13, wherein the electric dipole moments in different fibers are oriented in the same direction.

15. A piezoelectric component according to claim 13, further comprising a matrix polymer.

16. A piezoelectric component according to claim 13 which is a film.

17. A piezoelectric component according to claim 16, wherein the polymer fibers are oriented parallel to a surface of the film.

18. An electronic device comprising a piezoelectric fiber according to claim 1.

19. An electronic device according to claim 18, wherein said electronic device is at least one of a transducer, nanoswitch, cantilever, actuator, sensor, vector sensor, array sensor, microphone, speaker, and an energy harvesting device.

20. An electronic device comprising a piezoelectric component according to claim 13.

21. An acoustic sensor comprising a plurality acoustic transducers, wherein said plurality of acoustic transducers are structured and arranged to detect a corresponding plurality of vector components of an acoustic signal, and
   wherein at least one of said plurality of acoustic transducers comprises a piezoelectric fiber.

22. An acoustic sensor according to claim 21, wherein said piezoelectric fiber comprises a polypeptide, wherein molecules of said polypeptide have electric dipole moments that are aligned such that said piezoelectric fiber provides a piezoelectric effect at an operating temperature.

* * * * *